(12) United States Patent
Hauger et al.

(10) Patent No.: US 7,649,681 B2
(45) Date of Patent: Jan. 19, 2010

(54) SURGICAL MICROSCOPE

(75) Inventors: Christoph Hauger, Aalen (DE); Ulrich Gold, Aalen (DE); Christian Lücke, Oberkochen (DE); Margit Krause-Bonte, Aalen (DE); Dirk L. Brunner, Aalen (DE); Martin Pelzer, Zang (DE)

(73) Assignee: Carl-Zeiss-Stiftung, Oberkochen (DE)

( * ) Notice: Subject to any disclaimer, the term of this patent is extended or adjusted under 35 U.S.C. 154(b) by 0 days.

(21) Appl. No.: 09/780,375

(22) Filed: Feb. 12, 2001

(65) Prior Publication Data

US 2001/0024319 A1    Sep. 27, 2001

(30) Foreign Application Priority Data

Feb. 11, 2000    (DE) ................. 100 06 095

(51) Int. Cl.
*G02B 21/36*    (2006.01)
(52) U.S. Cl. ................. 359/363; 359/369; 359/630; 348/79
(58) Field of Classification Search ................. 359/363, 359/369, 629–640, 889, 660; 353/76, 101; 348/79, 5, 6; 349/5, 6; 396/296, 373
See application file for complete search history.

(56) References Cited

U.S. PATENT DOCUMENTS

| 4,090,219 | A | * | 5/1978 | Ernstoff et al. | ............... 348/742 |
| 4,240,701 | A | * | 12/1980 | Lytle | ............... 359/715 |
| 4,502,075 | A | * | 2/1985 | De Forest et al. | ............ 348/79 |
| 4,666,261 | A | * | 5/1987 | Arai | ............... 359/780 |
| 4,742,388 | A | * | 5/1988 | Cooper et al. | ............... 348/223 |
| 4,786,154 | A |   | 11/1988 | Fantone et al. | |
| 5,601,549 | A | * | 2/1997 | Miyagi | ............... 606/4 |
| 5,867,308 | A | * | 2/1999 | Pensel et al. | ............... 359/368 |
| 5,889,611 | A | * | 3/1999 | Zonneveld | ............... 359/376 |
| 5,953,114 | A | * | 9/1999 | Spink et al. | ............... 356/152.1 |
| 5,969,803 | A | * | 10/1999 | Mercado | ............... 355/67 |
| 6,081,371 | A | * | 6/2000 | Shioda et al. | ............... 359/369 |

FOREIGN PATENT DOCUMENTS

| DE | 36 23 394 | 4/1987 |
| DE | 199 01 963 | 8/1999 |
| EP | 0418109 | 3/1991 |
| EP | 0 475 502 | 3/1992 |
| EP | 0928981 | 7/1999 |

* cited by examiner

*Primary Examiner*—Lee Fineman
(74) *Attorney, Agent, or Firm*—Walter Ottesen

(57) ABSTRACT

A surgical microscope (1) includes a viewing unit (3) for viewing an object (5) and an image projection module (7) for inputting image data (9) into the viewing unit (3). The image projection module (7, 107, 207, 307) includes a plano-convex lens and a plano-concave lens. The image projection module (7, 107, 207, 307) includes an image display unit (11, 111, 211, 311).

12 Claims, 4 Drawing Sheets

SURGICAL MICROSCOPE

FIELD OF THE INVENTION

The invention relates to a surgical microscope having a viewing unit for viewing an object and having an image projection module for inputting image data into the viewing unit. The image projection module includes an image display unit.

BACKGROUND OF THE INVENTION

A surgical microscope of the above kind is disclosed, for example, in U.S. Pat. No. 5,095,887. This surgical microscope is configured as a stereomicroscope and includes an image projection module for reflecting endoscopic images into the ocular of the surgical microscope. For this purpose, the image projection module includes beam splitters which can be brought into the parallel viewing beam path of the surgical microscope. With the interaction of a shutter, the microscope user can either observe the microscope image by itself or the endoscope image by itself or a superposition of the microscope and endoscope images.

U.S. Pat. No. 5,601,549 discloses a surgical microscope wherein the image projection module includes a display screen. Several possibilities for arranging the display screen are shown in this publication.

A further surgical microscope is disclosed in U.S. Pat. No. 6,081,371. This surgical microscope includes an image recording module with a television camera for recording an image of the object supplied by the viewing unit.

SUMMARY OF THE INVENTION

It is an object of the invention to provide a surgical microscope of the kind described above which is improved with respect to the display of external image data.

The surgical microscope of the invention includes: a viewing unit for viewing an object; an image projection module for inputting image data into the viewing unit; the image projection module including an image display unit for displaying the image data; and, the image projection module including a plano-convex lens and a plano-concave lens mounted downstream of the image display unit.

The image display unit can be coupled into the viewing beam path of the surgical microscope with excellent imaging power because of the plano-convex lens and the plano-concave lens of the image projection module.

An especially good correction of astigmatism, coma and distortion and an especially good image field flattening can be achieved when the ratio of the focal length of the plano-convex lens and the magnitude of the focal length of the plano-concave lens is greater than 1.9 and less than 2.5.

According to one embodiment, the image projection module includes a beam splitter mounted in the viewing beam path of the viewing unit. A plano-convex lens, a plano-concave lens, a concave-convex lens and a further plano-convex lens are all mounted between the image display unit and the beam splitter. The relatively large number of planar lens surfaces of this embodiment results in favorable manufacturing costs.

According to another embodiment, the image recording module is configured in the surgical microscope of the invention so that the image data, which are supplied from the image projection module, can be recorded together with the image of the object which is supplied by the viewing unit. In this way, a video documentation is possible for a surgical microscope-supported surgical intervention wherein the images are recorded as they are seen by the user of the surgical microscope.

When the image projection module is mounted in the beam path of the surgical microscope between the object and the image recording beam splitter, a simultaneous recording of surgical microscope image and additional information, which is reflected into the surgical microscope, is possible in a structurally simple manner.

In this embodiment, the image recording beam splitter can be mounted outside of the viewing beam path whereby a further viewer can use the surgical microscope via the image recording beam splitter.

The image recording module can also include an image mixer, which mixes the image data, which are shown by the image projection module, and the image detected by the image sensor and can supply the same, for example, to a video recorder or monitor.

A further embodiment of the surgical microscope of the invention provides that the image display unit includes a time-dependent sequential reflection display illuminated with different colors. Such a sequential reflecting color display of this kind is superior to the conventional transmissive and emissive displays with respect to structural size, brightness and fill factor. These conventional transmissive and emissive displays are disclosed, for example, in U.S. Pat. No. 6,081,371.

The color generation takes place via sequential illumination of the display with basic colors RGB (red, green, blue). As a light source, red, green and blue LEDs are, for example, suitable or even the surgical microscope illumination with a rotating filter wheel which has red, green and blue filters. The rotation of the filter wheel is advantageously synchronized with the clock rate of the reflection display.

When superposing microscope image and external image data, the brightness of the external image data must be as high as possible in view of the typically bright image of the surgical microscope. This is achieved in the reflection display of the invention by a time-dependent sequential illumination of the reflection display with only a single color. In lieu of a sequential RGB illumination, a sequential GGG illumination is carried out, that is, illumination is exclusively, for example, with green LED or via the green filter.

When changing the illustration mode from the superposed mode of illustration to the exclusive illustration of either the microscope image or the external image data, an automatic switchover from GGG illumination to RGB illumination can be advantageously provided.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
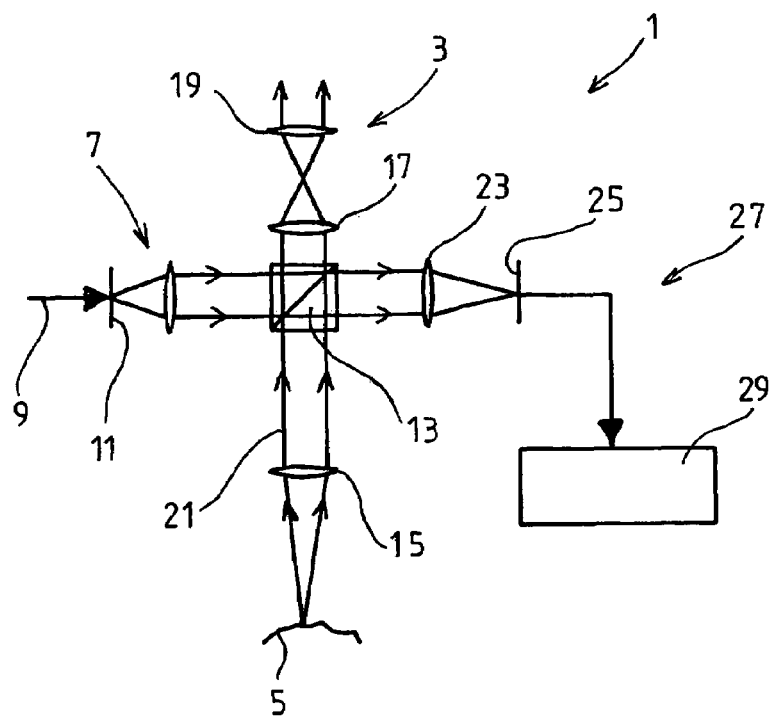
FIG. 1 is a schematic of the surgical microscope according to an embodiment of the invention.

In FIG. 1, a surgical microscope 1 includes a viewing unit 3 for viewing an object 5 and an image projection module 7 for inputting image data 9 into the viewing unit 3. The image projection module 7 comprises an image display unit 11 with which external image data 9 can be coupled in via a beam splitter 13 into the viewing unit 3. The image data 9 can, for example, be preoperatively generated diagnostic images, patient data or intraoperative ultrasonic images or endoscope images.

The viewing unit 3 includes an objective 15, a tubular lens 17 and an ocular 19. The viewing beam path 21 provides parallel beam rays between objective 15 and tubular lens 17. The beam splitter 13 is mounted in this parallel beam path 21 and images coming from the object 5 and from the image display unit 11 onto an image sensor 25 via an imaging optic 23. The image sensor 25 is part of an image recording module 27 and transmits the detected image to a video monitor 29 on which the image is shown and recorded.

One can switch over between different modes of viewing in the surgical microscope 1 by means of an LCD shutter, mechanical diaphragms or by switching off the surgical microscope illumination. These viewing modes include, for example, a microscope image by itself or external image data alone or a superposition of microscope and external image data or a juxtaposition of microscope image and external image data as also disclosed in U.S. Pat. No. 5,095,887.

Figure 2:
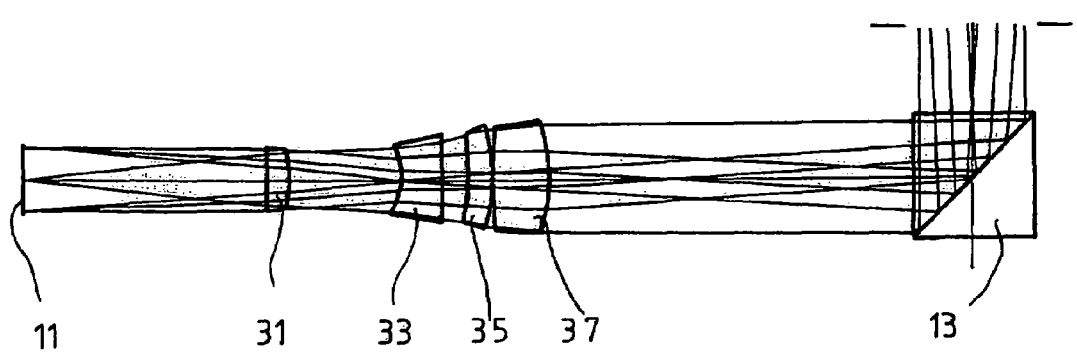
FIG. 2 is a detailed view of the optical components of the projection module of FIG. 1.

In FIG. 2, the optical components of the image projection module 7 are shown in detail.

In FIG. 2, a plano-convex lens 37, a plano-concave lens 33, a concave-convex lens 35 and a further plano-convex lens 31 can be seen. The following relationship of the focal width $f_{33}$ of the plano-concave lens 33 and the focal length $f_{37}$ of the plano-convex lens 37 is especially advantageous:

$$1.9*|f_{33}| < f_{37} < 2.5*|f_{33}|.$$

The Tables 1 and 2 provide detailed optical data for such imaging systems which are especially suited for an image display unit configured as an LCD and having a diagonal length of 9.4 mm.

The curvature radii in mm shown in FIG. 1 and the distances measured on the optical axis and/or lens thicknesses in mm as well as the types of glass can all be taken from these tables. The types of glass can be obtained from Schott Glas of Mainz, Germany, under the product identification given therefor in the tables.

A change of the imaging scale of the image display unit 11 in the intermediate image plane of the surgical microscope 1 can be achieved via a Galileo system comprising a diverging lens and converging lens. In this way, the image display unit 11 is always optimally coupled into the viewing beam path 21 when there is a switchover of the display modes.

Figure 3:
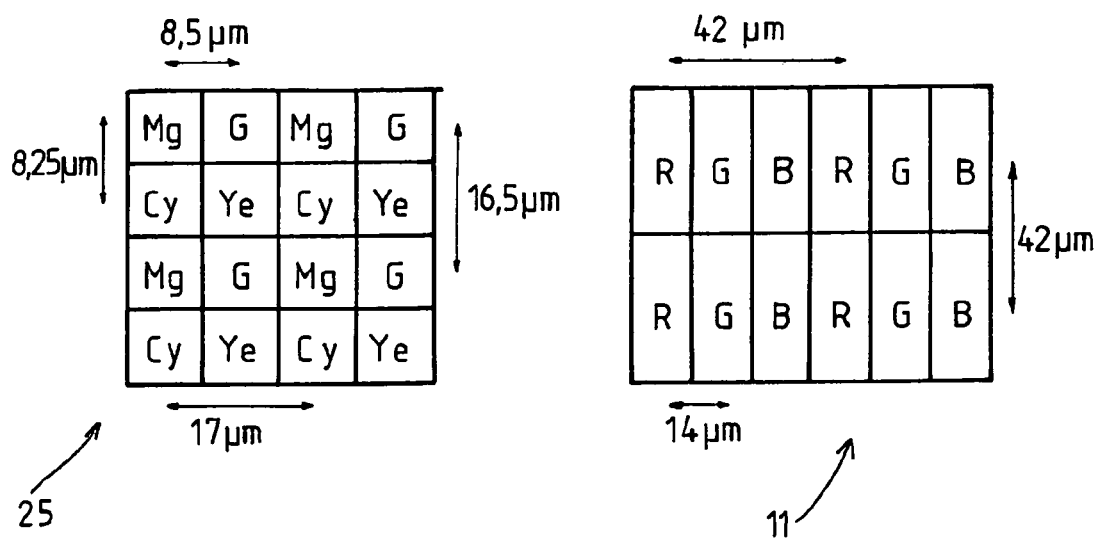
FIG. 3 is a detailed illustration of the image display unit and of the image sensor of FIG. 1.

The image display unit 11 is configured as an LCD and the image sensor 25 is configured as a CCD chip. To suppress Moiré-effects when imaging the image display unit 11 on the image sensor 25, the image display unit 11 and the image sensor 25 have the segment configuration shown in FIG. 3 with the segment configuration being subdivided into the different color segment regions.

A flickering in the superposition mode can be avoided by synchronizing the illumination of the image display unit 11 with the image sensor 25. The image display unit 11 is preferably configured as a reflective LCD.

Figure 4:
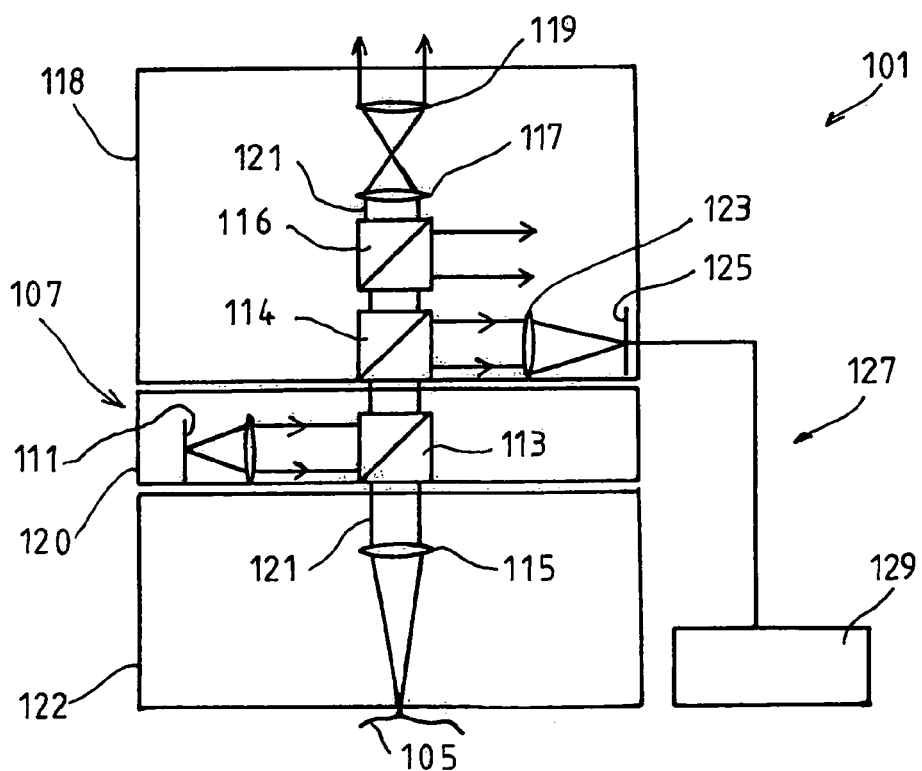
FIG. 4 is a schematic of a second embodiment of the surgical microscope according to the invention.

In FIG. 4, a second embodiment of the surgical microscope 101 is shown. The elements in FIG. 4 which correspond to the elements of FIG. 1 have the same reference numerals increased by 100. Reference can be made to the description of FIGS. 1 to 3 for an explanation of these elements.

In the surgical microscope 101, an image recording beam splitter 114 is mounted at the object side behind the beam splitter 113. In addition, a further beam splitter 116 for a further viewer is shown. It can be seen that the additional viewing person receives the complete image data presented to the primary viewer. The rectangular frames 118, 120 and 122 symbolize a modular configuration of the surgical microscope 101.

Figure 5:
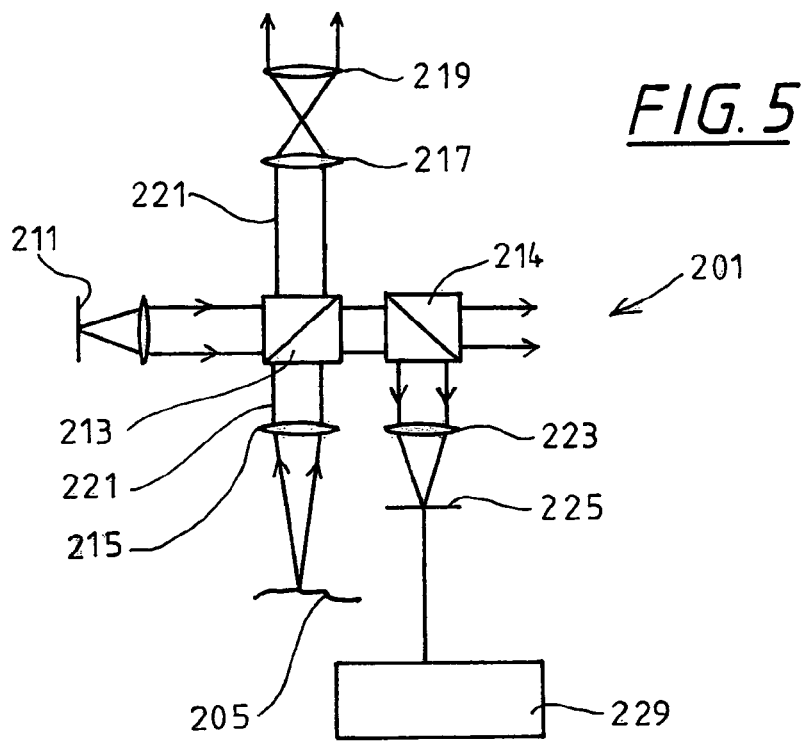
FIG. 5 is a schematic showing a third embodiment of the surgical microscope of the invention.

A third embodiment of the surgical microscope 201 is shown in FIG. 5. The elements in FIG. 5 which correspond to those elements in FIG. 1 have the same reference numerals but increased by 200. For a description of these elements, reference can be made to the descriptive material associated with FIGS. 1 to 3.

In the surgical microscope 201, an image recording beam splitter 214 is mounted on the object side behind the beam splitter 213 and outside of the viewing beam path 221. In this way, no separate beam splitter is required for a further viewer.

Figure 6:
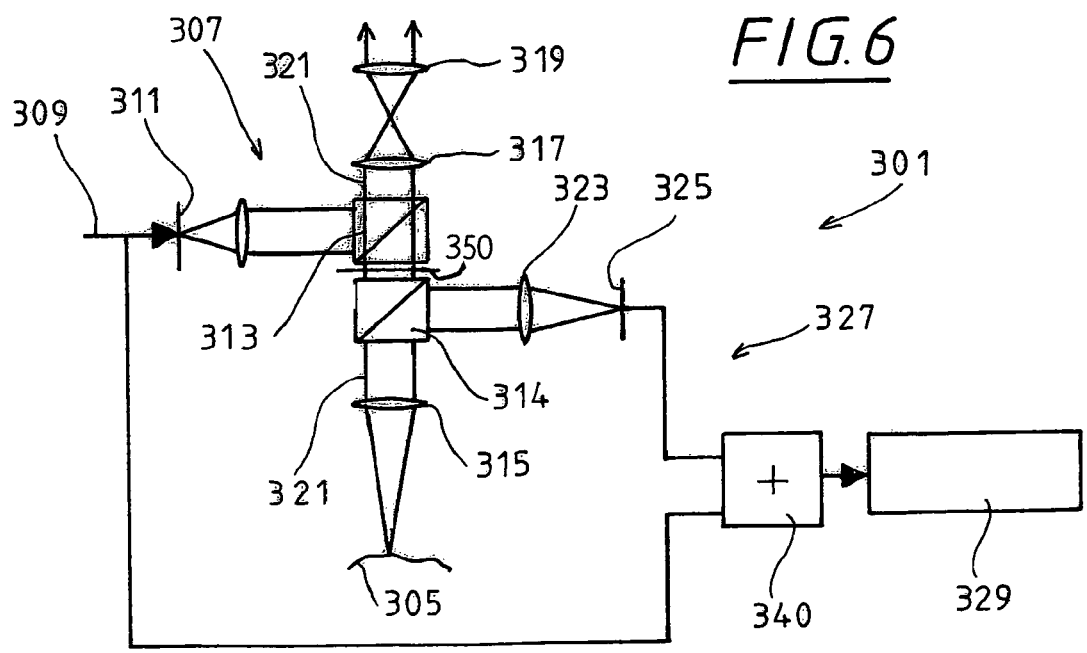
FIG. 6 is a schematic showing a fourth embodiment of the surgical microscope of the invention; and, FIG. 7 is a schematic showing a fifth embodiment of the surgical microscope of the invention.

A fourth embodiment of the surgical microscope 301 of the invention is shown in FIG. 6.

The elements in FIG. 6 which correspond to those elements of FIG. 1 have the same reference numerals but increased by 300. For a description of these elements, reference can be made to the descriptive material associated with FIGS. 1 to 3.

The image recording module 327 of the surgical microscope 301 includes an image mixer 340 which mixes the image data 309 displayed by the image projection module 307 and the image detected by the image sensor 325.

In the surgical microscope 301, the external image data 309 and the image of the object 305 can be combined by the mixer 340 in a suitable way and be made available via image display unit 311 to the primary and/or associate viewer. The direct image of the object 305 is suppressed by a shutter 350.

Figure 7:
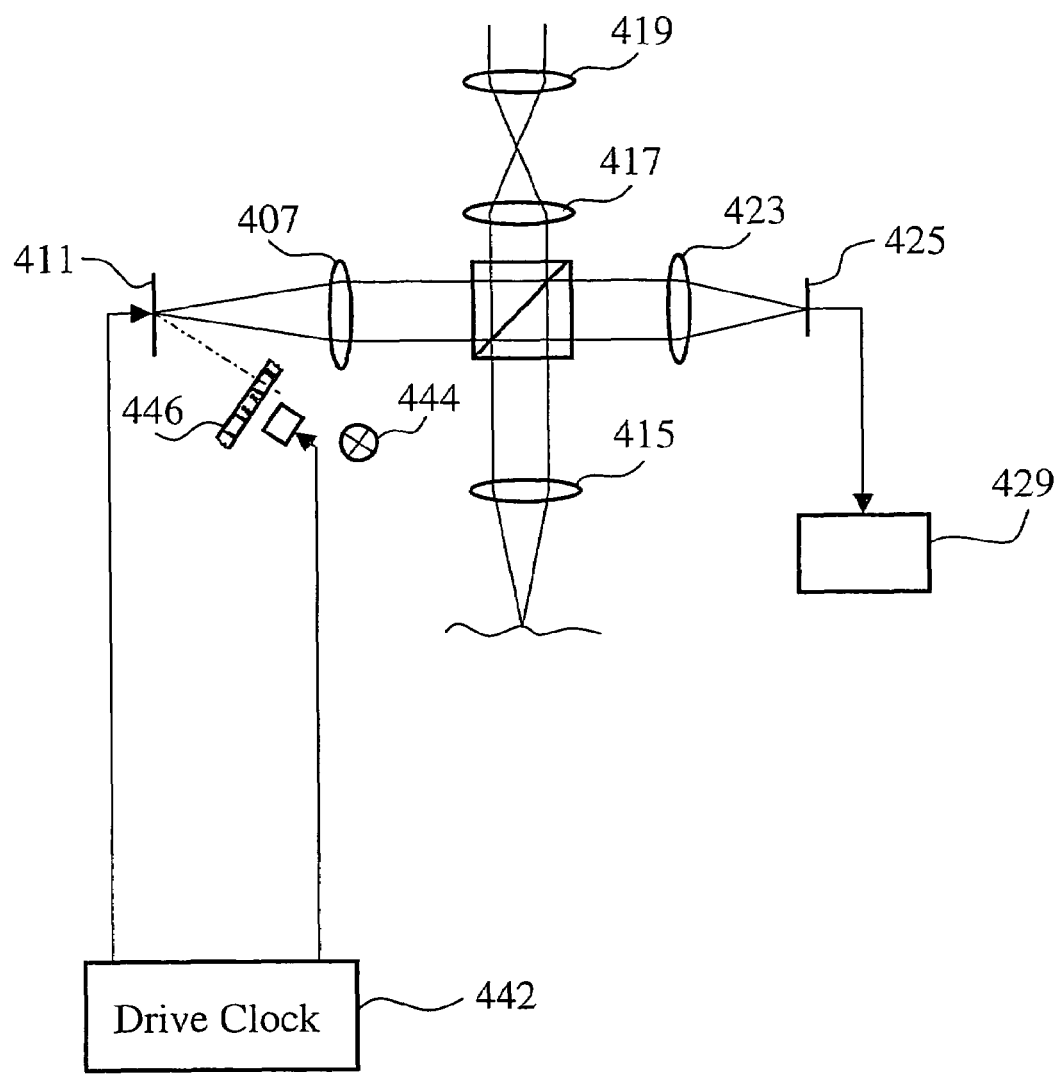

In FIG. 7, the image display unit 411 incorporates a reflection display driven at clock frequency by a drive clock 442. The drive clock 442 also drives a rotatably mounted filter wheel 446. An illuminating light source 444 emits light toward the reflection display of the image display unit 411 and this light passes through the filter wheel 446 as shown. The reflection display is driven at clock frequency and is illuminated sequentially with different colors utilizing the filter wheel. The image display can also be illuminated by a single color.

It is understood that the foregoing description is that of the preferred embodiments of the invention and that various changes and modifications may be made thereto without departing from the spirit and scope of the invention as defined in the appended claims.

TABLE 1

| No. | Radius | Thickness | Glass |
|---|---|---|---|
| 1 | Planar | 36.59 | |
| 2 | -48.3480 | 3.00 | N-LAF7 |
| 3 | -17.1540 | 16.26 | |
| 4 | Planar | 6.50 | SF1 |
| 5 | -36.2560 | 4.10 | |
| 6 | -24.7600 | 3.50 | N-PSK53 |
| 7 | Planar | 0.10 | |
| 8 | -30.2870 | 8.00 | N-PSK53 |

TABLE 2

| r1 | Planar  | 31.01 |       |
|----|---------|-------|-------|
| r2 | −60.43  | 3.00  | N-LAF7 |
| r3 | −16.909 | 24.91 |       |
| r4 | Planar  | 6.00  | SF1   |
| r5 | −59.566 | 3.40  |       |
| r6 | −26.799 | 3.50  | N-SK2 |
| r7 | Planar  | 0.10  |       |
| r8 | −29.007 | 5.00  | N-SK2 |

What is claimed is:

1. A surgical microscope comprising:

an ocular through which an object can be viewed;

a tubular lens disposed between said ocular and said object;

an objective disposed between said tubular lens and said object;

said tubular lens and said objective conjointly defining a parallel beam path along which parallel beam rays pass;

an image data supply for supplying image data;

an image projection module connected to said image data supply and including an image display unit for displaying said image data;

said image projection module further including a lens assembly for transmitting said image data to said parallel beam path;

a first beam splitter mounted in said parallel beam path for receiving all of said parallel beam rays;

said first beam splitter being disposed between said tubular lens and said objective for receiving said image data transmitted from said display unit and passing said image data into said parallel beam path;

an image recording module for recording said image data and an object image of said object;

said image recording module including an image sensor;

a second beam splitter mounted in said parallel beam path for likewise receiving said parallel beam rays;

said second beam splitter being disposed between said first beam splitter and said objective for receiving said object image directly from said objective and for directing said object image from said parallel beam path onto said image sensor;

said first and second beam splitters being the only beam splitters mounted in said parallel beam path;

said image sensor generating an image signal from said object image;

said image recording module further including a mixer connected to said image sensor for receiving said image signal and being connected to said image data supply for receiving said image data to mix said image signal and said image data and generate an output signal;

a video-recorder/monitor connected to said mixer for receiving said output signal for display to a surgeon; and, a shutter interposed between said first beam splitter and said object to suppress said object image to facilitate viewing said image data in said ocular without said object image.

2. The surgical microscope of claim 1, said lens assembly including an imaging optic having a plano-convex lens and a plano-concave lens mounted downstream of said image display unit for transmitting said image data to said first beam splitter.

3. Surgical microscope of claim 2, wherein said plano-concave lens is disposed downstream of said image display unit and said plano-convex lens is interposed between said plano-concave lens and said first beam splitter.

4. The surgical microscope of claim 3, wherein said image display unit is an LCD image display unit.

5. The surgical microscope of claim 4, wherein said plano-convex lens has a first focal length and said plano-concave lens has a second focal length; and, the ratio of said first focal length and said second focal length lies within a range from 1.9 to 2.5.

6. The surgical microscope of claim 5, wherein said plano-convex lens is a first plano-convex lens; said image projection unit further includes a concave-convex lens and a second plano-convex lens; and, said first plano-convex lens, said plano-concave lens, said concave-convex lens and said second plano-convex lens all are arranged between said LCD image display unit and said first beam splitter.

7. The surgical microscope of claim 4, wherein the brightness of said LCD image display unit is increased by providing a time-dependent sequential illumination of a reflection display with only a single color.

8. The surgical microscope of claim 4, wherein said LCD image display unit includes a reflection display illuminated sequentially with different colors as a function of time.

9. The surgical microscope of claim 1, wherein said image sensor is a CCD chip.

10. The surgical microscope of claim 1, wherein said image display unit incorporates a reflection display driven at a clock frequency and includes a rotatably mounted filter wheel for illuminating said reflection display; and, a device for synchronizing the rotation of said filter wheel with said clock frequency of said reflection display.

11. The surgical microscope of claim 1, wherein said image display unit has a reflection display driven at a clock frequency and includes a rotatably mounted filter wheel for illuminating said reflection display; and, a device for synchronizing the rotation of said filter wheel with said clock frequency of said reflection display.

12. The surgical microscope of claim 1, wherein said mixer is connected directly to said image data supply so as to receive said image data without said image data passing through one of said first and second beam splitters.

* * * * *

UNITED STATES PATENT AND TRADEMARK OFFICE
CERTIFICATE OF CORRECTION

PATENT NO. : 7,649,681 B2 Page 1 of 1
APPLICATION NO. : 09/780375
DATED : January 19, 2010
INVENTOR(S) : Christoph Hauger et al.

It is certified that error appears in the above-identified patent and that said Letters Patent is hereby corrected as shown below:

Column 3:
Line 12: add -- images -- after "images".

Signed and Sealed this

Thirteenth Day of April, 2010

David J. Kappos
*Director of the United States Patent and Trademark Office*